United States Patent [19]

Kampmann et al.

[11] Patent Number: 5,149,876
[45] Date of Patent: Sep. 22, 1992

[54] PROCESS FOR THE PREPARATION OF AMINES

[75] Inventors: Detlef Kampmann, Bochum; Jürgen Weber, Oberhausen; Helmut Bahrmann, Hamminkeln-Brünen; Claus Kniep, Oberhausen, all of Fed. Rep. of Germany

[73] Assignee: Hoechst Aktiengesellschaft, Fed. Rep. of Germany

[21] Appl. No.: 651,727

[22] Filed: Feb. 7, 1991

[30] Foreign Application Priority Data

Feb. 27, 1990 [DE] Fed. Rep. of Germany ....... 4006112

[51] Int. Cl.$^5$ ............................................ C07C 209/26
[52] U.S. Cl. ...................................... 564/467; 564/485
[58] Field of Search ................................ 564/485, 467

[56] References Cited

U.S. PATENT DOCUMENTS 3,502,725  3/1970  Dewhirst et al. ................... 564/485
4,142,060  2/1979  Kuntz ................................. 564/485
4,794,199 12/1988  Lin et al. ............................ 564/485

FOREIGN PATENT DOCUMENTS 0183648 10/1983  Japan ................................. 564/485
0210049 11/1984  Japan ................................. 564/485

Primary Examiner—Glennon H. Hollrah
Assistant Examiner—Scott C. Rand
Attorney, Agent, or Firm—Jordan B. Bierman

[57] ABSTRACT

A process for the preparation of amines by reaction of olefins with carbon monoxide, hydrogen, and a primary and/or secondary amine in the presence of rhodium and arylphosphines dissolved in water. Alkali metal salts, ammonium salts, and/or quaternary ammonium salts of sulfonated arylphosphines are used as the water-soluble arylphosphines.

26 Claims, No Drawings

PROCESS FOR THE PREPARATION OF AMINES

The present invention relates to a process for the preparation of amines by catalytic reaction of olefins with carbon monoxide, hydrogen, and a primary and/or secondary amine under elevated pressure and at elevated temperatures in the liquid phase. The compounds which serve as catalysts are those of the elements of group VIIIa of the IUPAC version of the Periodic Table of the Elements.

BACKGROUND OF THE INVENTION

A description of the reaction of olefins with amines, carbon monoxide, and water in the presence of transition metal catalysts containing, for example, rhodium, ruthenium or iridium, can be found in F. Jachimowicz and J. W. Raksis, J. Org. Chem. 1982, 47, pages 445 to 447. This process, also known as catalytic aminomethylation, produces amines in yields varying considerably and requires pure carbon monoxide as reactant.

GB 2,113,210 A relates to the preparation of tertiary amines by reaction of long-chain olefins with carbon monoxide, hydrogen, and a primary or secondary amine in the presence of a rhodium or ruthenium catalyst, in particular $RhCl_3.3H_2O$ and $RuCl_3.3H_2O$. A mono- or polygydric alcohol to which water may have been added is used as the solvent. After the reaction, the solvent phase containing the alcohol is separated off from the reaction product by phase separation, and the catalyst, most of which is dissolved in the solvent, is recovered. If the recovered catalyst is used again in the reaction, the yield of amine drops significantly after a few reuses. Since the reaction mixture still contains the expensive catalyst in non-negligible amounts, even after phase separation, the recovery of the catalyst effected by repeated separation of the solvent phase and its reuse as catalyst leaves something to be desired. Furthermore, a portion of the reaction product is present in the solvent phase and has to be separated in a further step.

BRIEF DESCRIPTION OF THE INVENTION

There is, therefore, a need for a process for the preparation of amines which avoids the above-mentioned disadvantages. This object is achieved by reaction of olefins with carbon monoxide, hydrogen, and a primary and/or secondary amine in the liquid phase in the presence of rhodium and arylphosphines at elevated temperature and pressure.

DETAILED DESCRIPTION OF THE INVENTION

The arylphosphines used are aqueous solutions of salts of the general formula

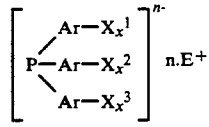

in which Ar is an aryl radical; and n is an integer from 1 to 3; X is a sulfo group; $x^1$, $x^2$, $x^3$ are 0 or 1, with the proviso that at least one of $x^1$, $x^2$, or $x^3$ is 1; E is an alkali metal atom, $NH_4$, or a quaternary ammonium ion of the general formula

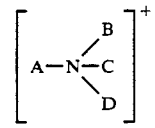

in which A is an alkyl radical having 6 to 20 carbon atoms; B, C, D are straight or branched chain alkyl radicals having 1 to 4 carbon atoms. The reaction is carried out at 100° to 160°, in particular 110° to 150°, preferably at 120° to 140° C., and at 4 to 20, in particular 8 to 18, preferably 10 to 16 MPa.

Surprisingly, it has been found that it is not necessary to use exclusively quaternary ammonium salts of sulfonated triarylphosphines as complexing ligands for rhodium to ensure that even the higher olefins can be converted successfully to the corresponding amines by the inventive process. Mixtures of alkali metal salts or ammonium salts and relatively small amounts of quaternary ammonium salts of the above-mentioned general formula are also suitable as complexing ligands for rhodium. The alkali metal salts of the water-soluble sulfonated triarylphosphines also include the ammonium compounds, i.e. salts containing the cation $NH_4^+$. It is particularly advantageous to work with sodium salts and/or potassium salts.

According to a preferred embodiment of the process according to the invention, the mixture of the water soluble phosphines contains 1 to 40, in particular 10 to 35, and preferably 15 to 33, mol % (based on the phosphine mixture) of quaternary ammonium salts.

The quaternary ammonium compounds used according to the invention are distinguished by containing a carbon-rich alkyl radical A and 3 short-chain alkyl radicals B, C, and D. Both the carbon-rich radical and the short-chain alkyl radicals can be branched or unbranched. Quaternary ammonium ions whose carbon-rich radical is a straight-chain alkyl radical having 10 to 18, in particular 12 to 16 carbon atoms, are preferred. Short-chain alkyl radicals are preferably methyl and/or ethyl radicals.

The preferred water soluble phosphines of the present invention are those in which Ar is phenyl or naphthyl, especially phenyl, and the sum of $x^1$, $x^2$, and $x^3$ is 2 or 3.

Examples of water-soluble phosphines which are suitable for carrying out the new process are sodium and/or potassium triphenylphosphinenetrisulfonates, and sodium and/or potassium triphenylphosphinedisulfonates, and tetraalkylammonium salts of the triphenylphosphanesulfonates mentioned having the following cations: trimethylcetylammonium, trimethyldodecylammonium, trimethyltetradecylammonium, trimethylhexadecylammonium, and dodecylethyldimethylammonium.

The phosphines used in the process claimed are prepared using sulfonated triarylphosphines as starting materials. These materials are obtained by treatment of triarylphosphines with oleum. By varying the reaction conditions, in particular the reaction time, temperature, and triarylphosphine to sulfur trioxide ration, it is possible to prepare preferentially mono-, di-, or trisulfonated arylphosphines.

Advantageously, amine salts of the sulfonation product which are insoluble in water but soluble in organic solvents are first prepared. They are then converted to the desired onium salt of the sulfonated triarylphosphine by treatment with a quaternary ammonium hydroxide. The reaction of the olefins with hydrogen, carbon monoxide, and amine in accordance with the new process takes place at elevated temperatures and pressures.

The catalyst can be preformed and then added to the reaction system. However, it can just as well be prepared from the components rhodium or a rhodium compound and an aqueous solution of the salts of the sulfonated triarylphosphines under the reaction conditions in the reaction mixture, i.e. in the presence of synthesis gas, amine, and olefin. Apart from metallic rhodium in finely divided form, it is also possible to use, as the source of rhodium, water-soluble rhodium salts (such as rhodium chloride, rhodium sulfate, rhodium acetate), or rhodium compounds soluble in organic media (such as rhodium 2-ethylhexanoate), or insoluble compounds, such as rhodium oxide.

The rhodium concentration in the aqueous catalyst solution is advantageously 10 to 2000 ppm by weight, preferably 50 to 800 ppm by weight, based on the aqueous solution. The quaternary ammonium salt of the sulfonated phospine is advantageously used in such an amount that 2 to 300 mol, preferably 10 to 100 mol, of phosphine compound is used per gram atom of rhodium.

The pH of the aqueous catalyst solution should not be below 2. In general, a pH of 2 to 13, preferably 5 to 7, has been found desirable.

The composition of the synthesis gas, i.e. the ratio of carbon monoxide to hydrogen, can be varied within wide limits. In general, a synthesis gas is used in which the volume ratio of carbon monoxide to hydrogen is 1:1 to 1:2.5 or deviates from this value only slightly. 1 to 12, in particular 1.2 to 10, preferably 1.5 to 8, mols of CO, and 2 to 24, in particular, 2.4 to 20, preferably 3 to 16, mols of $H_2$ are used per mol of olefin. It has proven suitable to work with an excess of 10 to 200, in particular 25 to 120, mol % of CO and 20 to 400, in particular 50 to 240, mol % of $H_2$, per mol of olefin.

The primary and/or secondary amine required for the reaction is used in an amount of 1 to 3, in particular 1 to 2, and preferably 1 to 1.5, mols per mol of olefin to be reacted. Suitable amines are aliphatic, straight or branched chain primary or secondary amines having 1 to 24, in particular 2 to 12, preferably 2 to 8, carbon atoms. Mixtures of these amines may also be used. Secondary amines of the formula $R_1R_2NH$ in which $R_1$ and $R_2$ are identical or different and each contain 1 to 4 carbon atoms, in particular dimethyl-, diethyl- and methylethylamines, have proven particularly suitable. Methyl, ethyl, and propyl amines, in particular methyl and ethyl amines, can advantageously be used as primary amines.

The reaction can be carried out either batchwise or continuously. After the reaction is completed, the reaction mixture is, if required, cooled, and the aqueous bottom phase containing the catalyst system comprising rhodium and salts of sulfonated triarylphosphines is separated from the organic top phase.

A particular advantage of the process according to the invention is that the aqueous catalyst solution, after being separated, can be used again successfully in the reaction. The effectiveness of the recycled aqueous catalyst phase gradually decreases but only after multiple reuses. If it is desired to improve the life of the used aqueous catalyst solution even more, it is recommended that a small amount of fresh catalyst be added to increase not only its activity but also its selectivity.

This advantage can be exploited with particular ease in a continuous operation by transferring the mixture composed of the organic product and the aqueous catalyst solution directly to a phase separation tank, separating the aqueous phase continuously, if desired, adding a suitable amount of fresh catalyst, and returning the mixture to the reaction zone. This recirculating procedure is particularly easy on the catalyst and ensures an increased life of the used catalyst solution. The catalyst losses caused by separating the organic valuable products are relatively small. They are about 0.1% to 1% by weight of Rh per cycle.

The process according to the invention can be successfully applied to the reaction of straight or branched chain olefins having 2 to 24, in particular 8 to 20, preferably 12 to 18, carbon atoms. For best results, the double bond in these olefins should be terminal. Suitable olefins are n-hexene-1, n-heptene-1, n-octene-1, n-nonene-1, n-decene-1, n-dodecene-1, n-tetradecene-1, n-hexadecene-1, in particular n-decene-1, n-dodecene-1, and n-tetradecene-1.

The examples which follow illustrate the invention in more detail without limiting it to the embodiments described.

PREPARATION OF THE CATALYST SOLUTION

An aqueous solution containing the sodium salts of triphenylphosphine-m-disulfonic acid (TPPDS-Na), of triphenylphosphine-m-trisulfonic acid (TPPTS-Na), an onium salt and rhodium acetate corresponding to 200 ppm of Rh are initially introduced into an autoclave equipped with an immersion tube. The phosphorus/rhodium ratio is 300:1, the ratio of TPPDS-Na to TPPTS-Na is 1:(14 to 15), and the onium salt and sodium salt ratio is about 1:2.

Synthesis gas ($CO/H_2=1:1$) is then injected into this solution to a pressure of 10 MPa. The mixture is heated to 125° C. with stirring and the aqueous solution is treated with synthesis gas for 3 hours. It is cooled to about 30° C., the stirring is discontinued and, after a settling time of about 15 minutes, the excess solution is forced out via the immersion tube. The rest of the catalyst solution remains in the autoclave.

EXAMPLES 1 to 10

118 g (about 0.7 mol) of dodecene and 50 g (1.11 mol) of dimethylamine are pumped into 400 g of the catalyst solution described above, which contains the n-tetradecyltrimethylammonium salt as the onium salt. The reaction is carried out at 140° C. and 10 MPa with stirring, the synthesis gas being replenished as it is consumed.

After about 4 hours, the absorption of synthesis gas stops. The mixture is allowed to continue reacting for a further hour, cooled and, after a settling time of 15 minutes, the organic phase is forced out via the immersion tube. This is followed by again pumping in the above-mentioned amounts of n-dodecene and dimethylamine, and the reaction as described above is repeated. The organic phase formed in each case is weighed and analyzed by gas chromatography. The results obtained therefrom can be seen in Table 1.

TABLE 1

| Example[1] | | 1 | 2 | 3 | 4 | 5 | 6 | 7 | 8 | 9 | 10 |
|---|---|---|---|---|---|---|---|---|---|---|---|
| Conversion[2] | (%) | 94.5 | 94 | 90.25 | 87.97 | 81.59 | 81.66 | 79.39 | 77.01 | 81.69 | 75.6 |
| Selectivity[2] | (%) | 78 | 84.9 | 91.2 | 92.8 | 94.3 | 93.5 | 93.5 | 93.5 | 92.1 | 94.2 |
| n:iso ratio[3] | (n) | 58 | 65 | 70 | 71 | 72 | 73 | 71 | 70 | 71 | 72 |
| | (iso) | 42 | 35 | 30 | 29 | 28 | 27 | 29 | 30 | 29 | 28 |
| Yield[2] | (%) | 73.7 | 79.8 | 82.4 | 81.7 | 77.0 | 76.4 | 74.2 | 72.0 | 75.2 | 71.2 |

[1] Examples 2 to 10 were carried out with reused catalyst solution from Example 1
[2] Relative to olefin used
[3] Ratio of N,N-dimethyl-n-tridecylamine:N,N-dimethyl-2-methyldodecylamine

What we claim is:

1. A process for the preparation of aliphatic secondary and/or tertiary amines comprising a reaction of an olefin with carbon monoxide, hydrogen, and a primary and/or secondary amine in a liquid phase, at elevated temperature and pressure, in the presence of rhodium and an aqueous solution of salts of arylphosphines of the formula

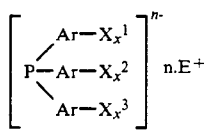

wherein Ar is an aryl radical; X is a sulfo group; $x^1$, $x^2$, $x^3$ are 0 or 1, with the proviso that at least one of $x^1$, $x^2$, or $x^3$ is 1; E is an alkali metal atom, $NH_4$, or a quaternary ammonium ion of the formula

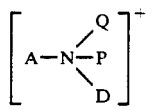

wherein A is a carbon rich alkyl radical having 6 to 20 carbon atoms, Q, R, D are individually straight or branched chain alkyl radicals having 1 to 4 carbon atoms, and n is an integer from 1 to 3.

2. The process of claim 1 wherein said temperature is 100° to 160° C., and said pressure is 4 to 20 Mpa.

3. The process of claim 2 wherein said temperature is 110° to 150° C., and said pressure is 8 to 18 MPa.

4. The process of claim 3 wherein said temperature is 120° to 140° C., and said pressure is 10 to 16 MPa.

5. The process of claim 1 wherein said arylphosphines are a mixture of alkali metal or ammonium salts, and quaternary ammonium salts of the formula

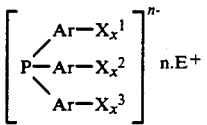

6. The process of claim 5 wherein 1 to 40 mol % of said quaternary ammonium salts, based on said mixture, is present.

7. The process of claim 1 wherein E is sodium or potassium.

8. The process of claim 1 wherein A has 10 to 18 carbon atoms.

9. The process of claim 8 wherein A has 12 to 16 carbon atoms.

10. The process of claim 1 wherein each of Q, R, and D is individually methyl or ethyl.

11. The process of claim 1 wherein said quaternary ammonium ion is selected from the group consisting of trimethyldodecylammonium, trimethyltetradecylammonium, and triethylhexadecylammonium.

12. The process of claim 1 wherein Ar is phenyl or naphthyl.

13. The process of claim 1 wherein said primary and/or secondary amine is present in an amine amount of 1 to 3 mols per mol of said olefin.

14. The process of claim 13 wherein said amine amount is 1 to 2 mols per mol of said olefin.

15. The process of claim 14 wherein said amine amount is 1 to 1.5 mols per mol of said olefin.

16. The process of claim 1 wherein said primary and/or secondary amine has 1 to 24 carbon atoms.

17. The process of claim 16 wherein said primary and/or secondary amine has 2 to 12 carbon atoms.

18. The process of claim 16 wherein said primary and/or secondary amine has 2 to 8 carbon atoms.

19. The process of claim 1 wherein said aqueous solution has a pH of 5 to 7.

20. The process of claim 1 wherein said carbon monoxide is present in an excess amount of 10 to 200 mol % based on said olefin.

21. The process of claim 1 wherein said hydrogen is present in an excess amount of 20 to 400 mol % based on said olefin.

22. The process of claim 1 wherein there are 1 to 12 mols of carbon monoxide per mol of said olefin.

23. The process of claim 1 wherein there are 2 to 24 mols of hydrogen per mol of said olefin.

24. The process of claim 1 wherein said olefin has 2 to 24 carbon atoms.

25. The process of claim 24 wherein said olefin has 8 to 20 carbon atoms.

26. The process of claim 25 wherein said olefin has 12 to 18 carbon atoms.

* * * * *